United States Patent [19]

Carter

[11] Patent Number: 5,074,291

[45] Date of Patent: Dec. 24, 1991

[54] HAND TRACTION SURGICAL TABLE

[76] Inventor: Peter R. Carter, 3419 Drexel Dr., Dallas, Tex. 75205

[21] Appl. No.: 583,457

[22] Filed: Sep. 17, 1990

[51] Int. Cl.⁵ .......................... A61F 5/04; A61G 13/00

[52] U.S. Cl. ................................ 128/84 R; 128/84 C; 269/328

[58] Field of Search ................ 128/84 R, 84 A, 84 C, 128/84 B, 87 R, 87 A, 77, 878, 879, 165, 882, 75; 269/328

[56] References Cited

U.S. PATENT DOCUMENTS

| | | | |
|---|---|---|---|
| 2,243,294 | 5/1941 | Stearns | 128/84 R |
| 2,515,590 | 7/1950 | Chaffin | 128/84 R |
| 2,691,979 | 10/1954 | Watson | 128/84 |
| 2,783,758 | 3/1957 | Trott | 128/84 |
| 2,796,061 | 6/1957 | Miller | 128/84 R |
| 3,149,630 | 9/1964 | Schmidt | 128/84 R |
| 3,390,675 | 7/1968 | Giannestras | 128/84 |
| 3,540,719 | 11/1970 | Romney et al. | 269/324 |
| 3,693,617 | 9/1972 | Trott | 128/84 |
| 3,714,940 | 2/1973 | Palmer | 128/87 A |
| 3,850,166 | 11/1974 | Tamny et al. | 128/84 |
| 3,872,861 | 3/1975 | Tamny et al. | 128/84 |
| 4,409,970 | 10/1983 | Carrel | 128/84 |
| 4,445,506 | 5/1984 | Johanssen et al. | 128/84 |
| 4,616,637 | 10/1986 | Caspari | 128/84 B |
| 4,651,719 | 3/1987 | Funk | 128/77 |
| 4,679,552 | 7/1987 | Caspari | 128/132 |
| 4,858,903 | 8/1989 | Tari et al. | 269/328 |
| 4,930,523 | 6/1990 | Laico | 128/84 R |
| 4,941,464 | 7/1990 | Scott | 128/84 R |

*Primary Examiner*—Robert A. Hafer
*Assistant Examiner*—Michael Brown
*Attorney, Agent, or Firm*—Richards, Medlock & Andrews

[57] ABSTRACT

A hand traction surgical table having an adjustable surgical table frame is provided. An arm board having an upper surface and a lower surface is mounted on the surgical table frame, thereby providing an operating surface for surgical procedures on the wrist and forearm. A pulley is mounted on the surgical table frame and a reduction force applying cable is mounted through the pulley. A finger retention device is mounted at a first end of the cable and a force applicator is mounted at a second end of the cable such that a predetermined reduction force can be applied to the patient's hand.

13 Claims, 4 Drawing Sheets

HAND TRACTION SURGICAL TABLE

TECHNICAL FIELD OF THE INVENTION

This invention relates to a hand traction surgical table for use in surgical procedures on the hand and forearm.

BACKGROUND OF THE INVENTION

Surgical procedures are commonly used to correct fractures to the bones of the hand and forearm. Fractures of the distal radius, commonly known as Colles' fractures, are among the most common fractures occurring in humans in the United States. Repair of a Colles' fracture may entail open reduction of the fracture and internal fixation of the fractured radius in order to stabilize the comminuted portions of the bone. Internal fixation requires the use of surgical procedures.

Due to the large number of bones, tendons, and muscles in the hand and forearm, surgical procedures affecting these areas require a high degree precision. These procedures are facilitated by the use of specialized operating surfaces which provide greater access to the hand and forearm during the surgical procedure. Such procedures are further facilitated through the use of specialized operating tables which retain the fractured bones of the hand and forearm in a "reduced" or corrected position throughout the surgical procedure.

Examples of fracture reducing devices are set forth in U.S. Pat. No. 3,693,617 to Trott, "Fracture Reducing Appliance for the Arm," (issued Sept. 26, 1972); U.S. Pat. No, 3,850,166 to Tamny, et al., "Fracture Reduction System," (issued Nov. 26, 1974); U.S. Pat. No. 4,409,970 to Carrel, "Apparatus and Method for Treatment of Comminuted Colles, Fracture," (issued Oct. 18, 1983); and U.S. Pat. No. 4,445,506 to Johansson, et al., "Bone Aligning Apparatus," (issued May 1, 1984). Each of these references provides a device for the reduction of fractures of the distal radius. However, the devices disclosed by Trott, Tamny, et al., Carrel, and Johansson, et al., do not orient the hand and forearm in such a way as to facilitate surgical procedures on the hand and forearm. The hand traction surgical table of the present invention provides a reduction force to the bones of the wrist such that the hand and forearm are maintained in a position in which they can be treated surgically.

A specialized operating surface for the hand and forearm preferably provides for the precise application of a predetermined reduction force which can be varied in accordance with the needs of the particular surgical procedure. The hand traction surgical table of the present invention is constructed to provide for the precise application of a predetermined reduction force to maintain the alignment of the fractured bone fragments while simultaneously retaining the hand and forearm in a standard surgical position, i.e., a position commonly used by orthopedic surgeons in hand and wrist surgery.

SUMMARY OF THE INVENTION

The hand traction surgical table of the present invention includes an arm board to be mounted on a table frame. A pulley carrying a traction cable is also mounted on the table frame. A finger retention device is mounted on one end of the traction cable in order to permit the traction cable to be connected to the hand and forearm of the patient during a surgical procedure. A force applicator is mounted on a second end of the tension cable such that a predetermined force can be applied to the tension cable.

BRIEF DESCRIPTION OF THE DRAWINGS

A more complete understanding of the present invention and its advantages will be apparent from the following detailed description read in conjunction with the accompanying drawings, in which.

DETAILED DESCRIPTION

Figure 1:
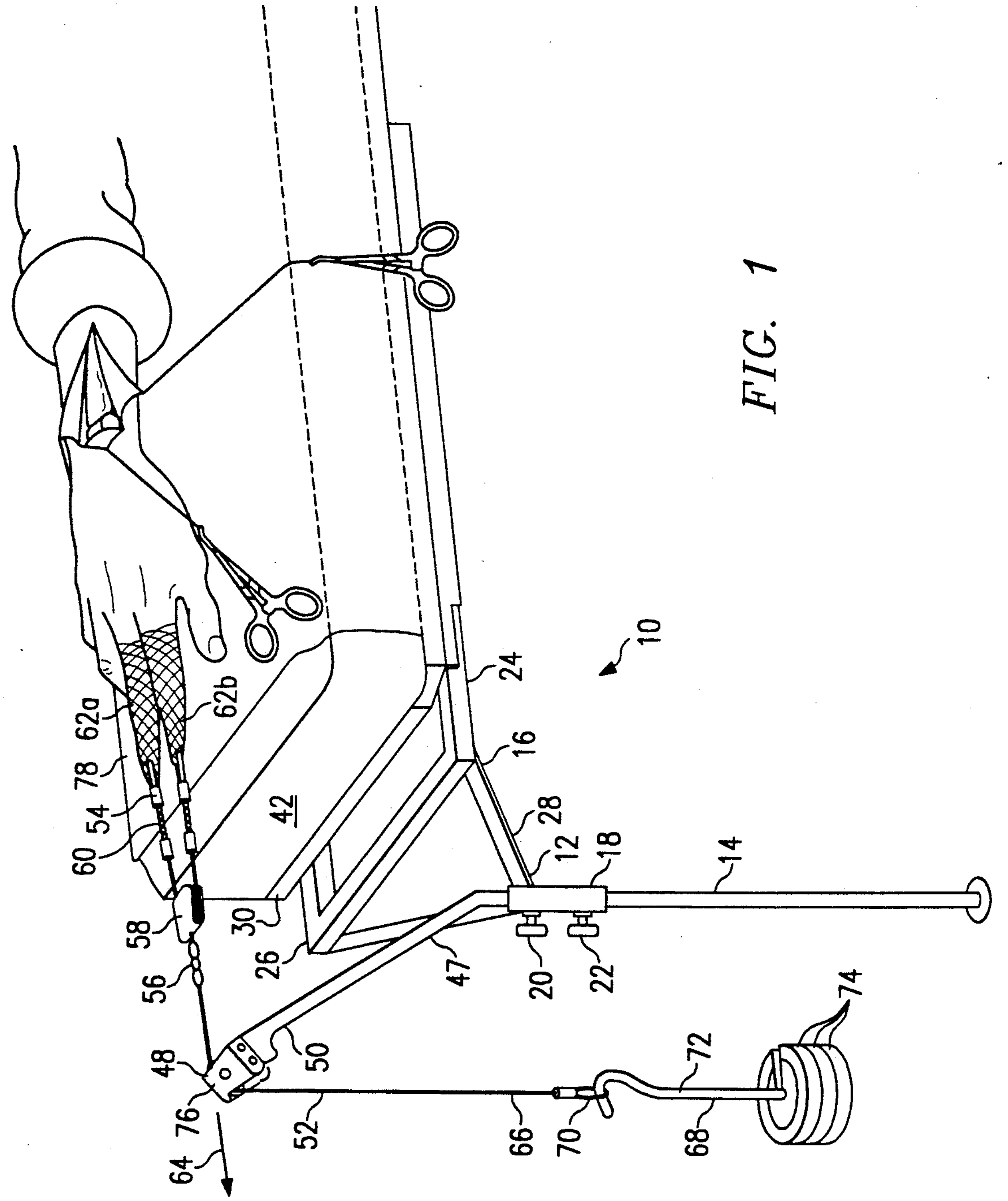
FIG. 1 is a plan view of the hand traction surgical table of the present invention.

The hand traction surgical table of the present invention is generally indicated at 10 of FIG. 1. Hand traction surgical table 10 includes frame !2. In the preferred embodiment depicted in FIG. 1, frame 12 includes support leg 14 and support frame 16. In order to provide for a variation in elevation of hand traction surgical table 10, tubular connector 18 is disposed on support frame 16. Connector 18 includes threaded fasteners 20, 22 which are disposed through connector 18. As depicted in FIG. 1, leg 14 is inserted into connector 18 and secured by tightening threaded fastener 22. It will be appreciated that the elevation of hand traction surgical table 10 can be adjusted by selectively positioning leg 14 within tubular connector 18.

In the preferred embodiment, support frame 16 includes support arms 24, 26 and triangular-shaped support section 28. Support arms 24, 26 are preferably constructed to be attachable to a primary surgical table on which the patient is positioned during a surgical procedure. Surgical tables commonly include arm board attachment elements or mounts, as depicted at 29 of FIG. 3.

Figure 2:
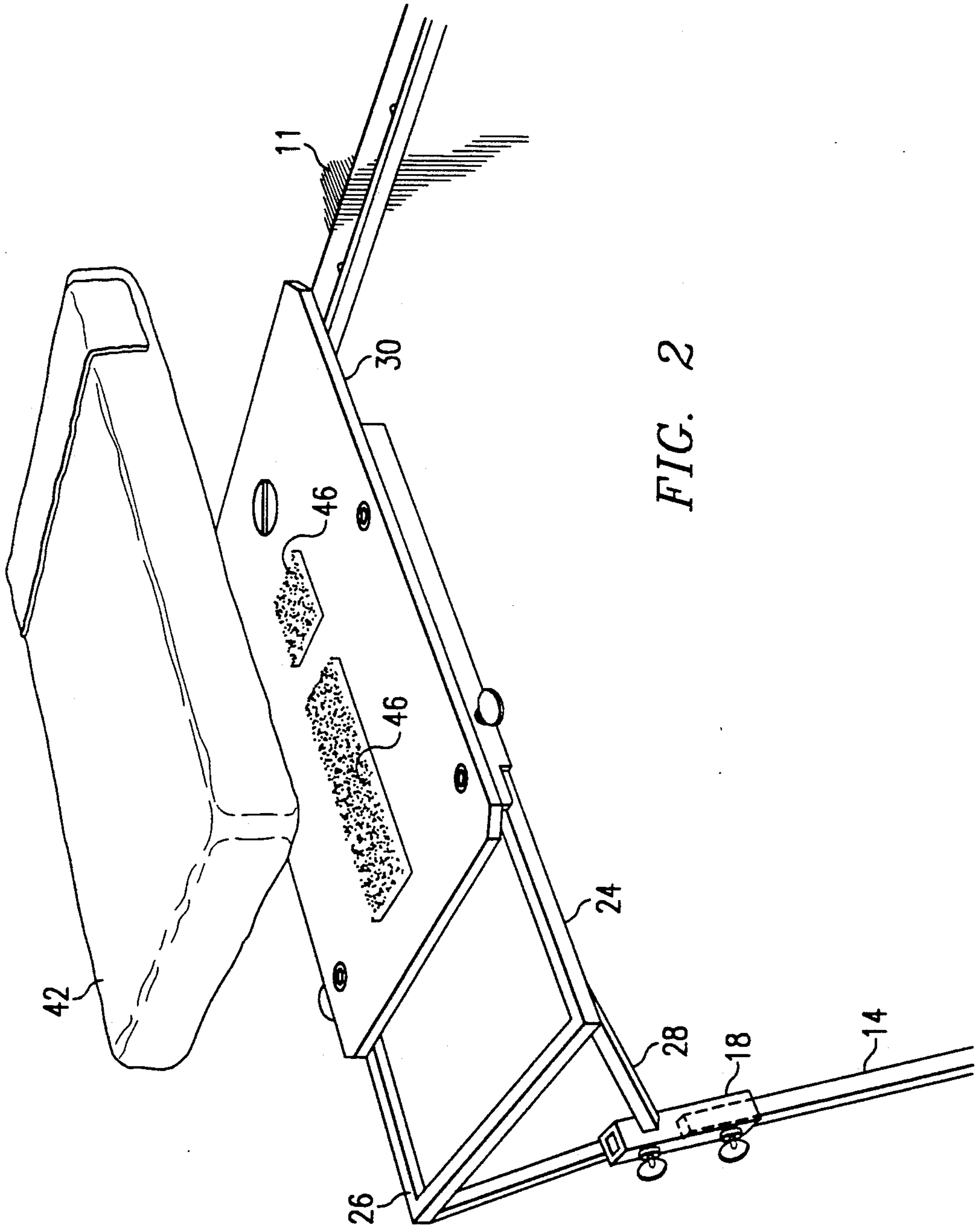
FIG. 2 is an exploded view of the hand traction surgical table of the present invention.
Figure 3:
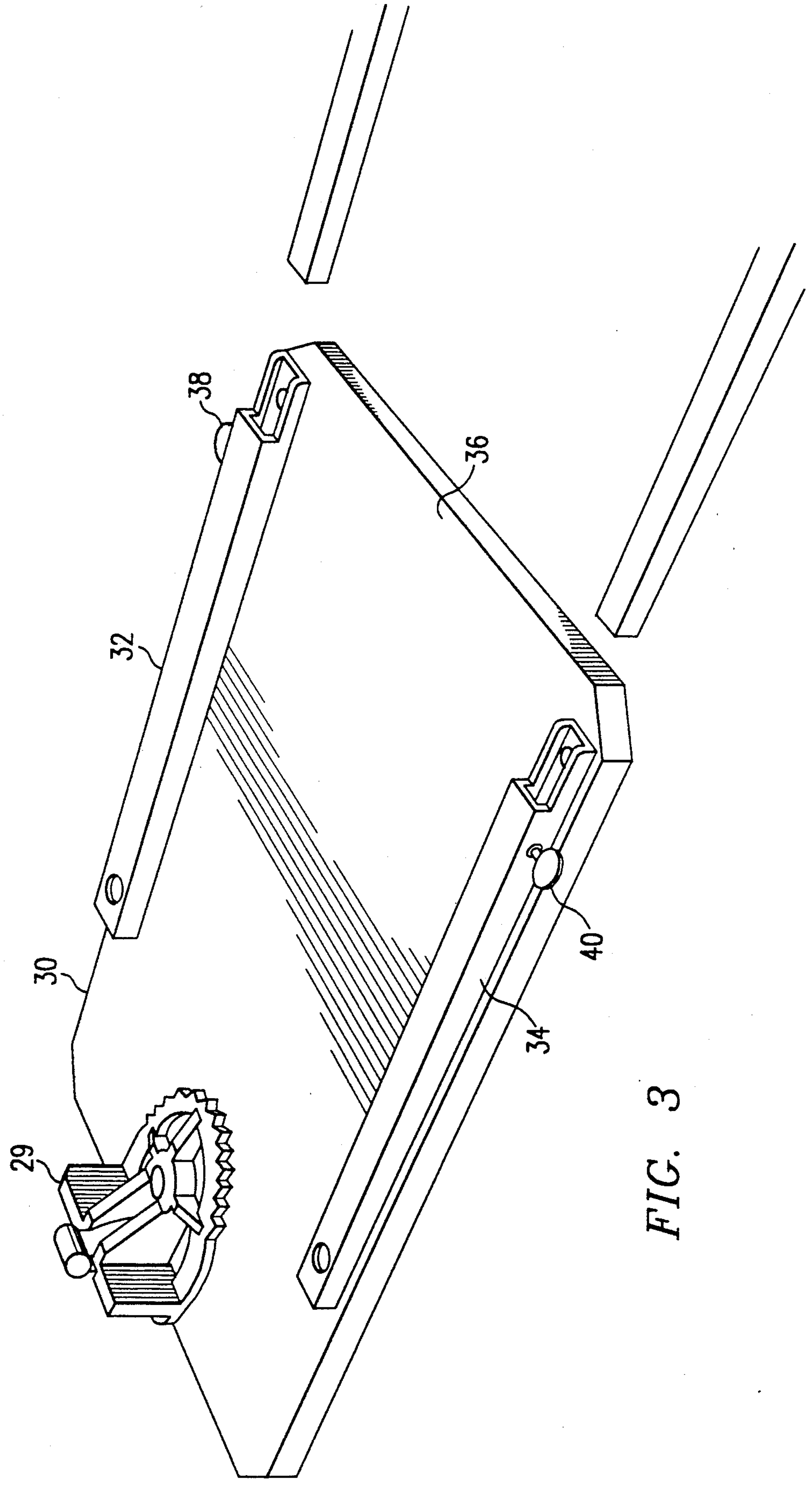
FIG. 3 is a bottom view of the arm board of the hand traction surgical table of the present invention.

An arm board 30 is mounted on arms 24, 26, as best seen in FIG. 2. In a preferred embodiment of the present invention, channels 32, 34 are disposed on underside 36 of arm board 30, as depicted in FIG. 3. In this way arm board 30 can be slidably mounted on arms 24, 26 through channels 32, 34, respectively. In this embodiment, arms 24, 26 can be adjustably disposed within channels 32, 34 at any desired location. Threaded fasteners 38, 40 are disposed through channels 32, 34 such that, when in a tightened condition, they engage arms 24, 26, respectively By tightening threaded fasteners 38, 40, arm board 30 is secured to arms 24, 26, thereby providing a stable operating surface. Arm board 30 is preferably constructed such that it can be mounted on the primary surgical table through arm board attachment element 29, as depicted in FIG. 3, thereby allowing the hand traction surgical table of the present invention to be unitary with the primary surgical table 11 during surgical procedures.

In a preferred embodiment of the present invention, arm board pad 42 is disposed on upper surface 44 of arm board 30 such that the hand traction surgical table of the present invention and the primary surgical table have the same elevation. Thus, it is to be appreciated that arm board pad 42 will have approximately the same thickness as any pad disposed on primary surgical table 11. In order to facilitate removal of arm board pad 42, hook and looptype fasteners 46 can be disposed on upper surface 44 and on arm board pad 42. In this way, pad 42 can be removed and replaced, thereby providing for the use of a sterile arm board pad during each surgical procedure performed on table 10. It is to be appreciated that any other known means for detachably mounting arm board pad 42 to arm board 30 can be used without departing from the scope of the present invention.

Pulley support arm 47 is mounted through connector 18. Threaded fastener 20 is disposed through connector 18 such that it engages support arm 47 when in its tightened position. Pulley 48 is disposed at distal end 50 of pulley support arm 47. Traction cable 52 is disposed through pulley 48 as depicted in FIG. 1. Finger retention device 54 is disposed at first end 56 of traction cable 52. In a preferred embodiment of the present invention, finger retention device 54 comprises a pair of Chinese finger traps, 62*a*, 62*b*. In another preferred embodiment of the present invention depicted in FIG. 1, finger retention device 54 includes pulley 58 and cable 60. In this embodiment, Chinese finger traps 62*a*, 62*b* are disposed at each end of cable 60. Chinese finger traps 62*a*, 62*b* are constructed to tighten about the patient's fingers as force is applied in the direction of arrow 64.

In a preferred embodiment of the present invention, traction cable 52, pulley 48, and pulley support arm 47 are constructed of stainless steel. The use of stainless steel in the construction of these elements allows them to be sterilized prior to their use in a surgical procedure. It will be appreciated that other materials can be used in the construction of cable 52, pulley 48, and arm 47 so long as such materials can be sterilized prior to use of the hand traction surgical table of the present invention.

In another preferred embodiment of the present invention, frame 12 and arm board 30 are constructed of a radiotransparent material in order to permit the surgeon to examine the fracture by means of X-ray during the surgical procedure on the hand and forearm.

Force applicator 68 is disposed at second end 66 of traction cable 52. In a preferred embodiment of the present invention, force applicator 68 includes a loop 70 formed at second end 66 of traction cable 52. In this preferred embodiment, force applicator 68 further includes platform 72 which can be mounted on traction cable 52 through loop 70. Platform 72 is constructed to receive weights 74. The quantity of weights 74 mounted on platform 72 will be dependent upon the magnitude of the reduction force desired by the surgeon. It has been found that forces in the range of 5–15 pounds provide optimal reduction of Colles' fractures Forces outside of this range may be also used, dependent upon the nature of the fracture or injury being treated.

In use, the patient is placed on primary surgical table 11 and the patient's arm is placed on the hand traction surgical table 10 as depicted in FIG. 1. Chinese finger traps 62*a*, 62*b* are secured on the fingers of the patient's hand. A predetermined weight is then applied to platform 72. The downward force of weights 74 is transposed by pulley 48 such that a reduction force in direction 64 is applied to the hand of the patient. This force effectively reduces the fracture. This reduction force preferably is maintained throughout the surgical procedure. It is to be appreciated that the true direction of the reduction force is dependent upon the elevation of highest point 76 of pulley 48. That is, if point 76 is below the level of upper surface 78 of arm board pad 42, the reduction force will have both horizontal and downward vector components. Conversely, if point 76 is substantially higher than the level of upper surface 78 of arm board pad 42, the reduction force will have both horizontal and upward vector components.

Figure 4:
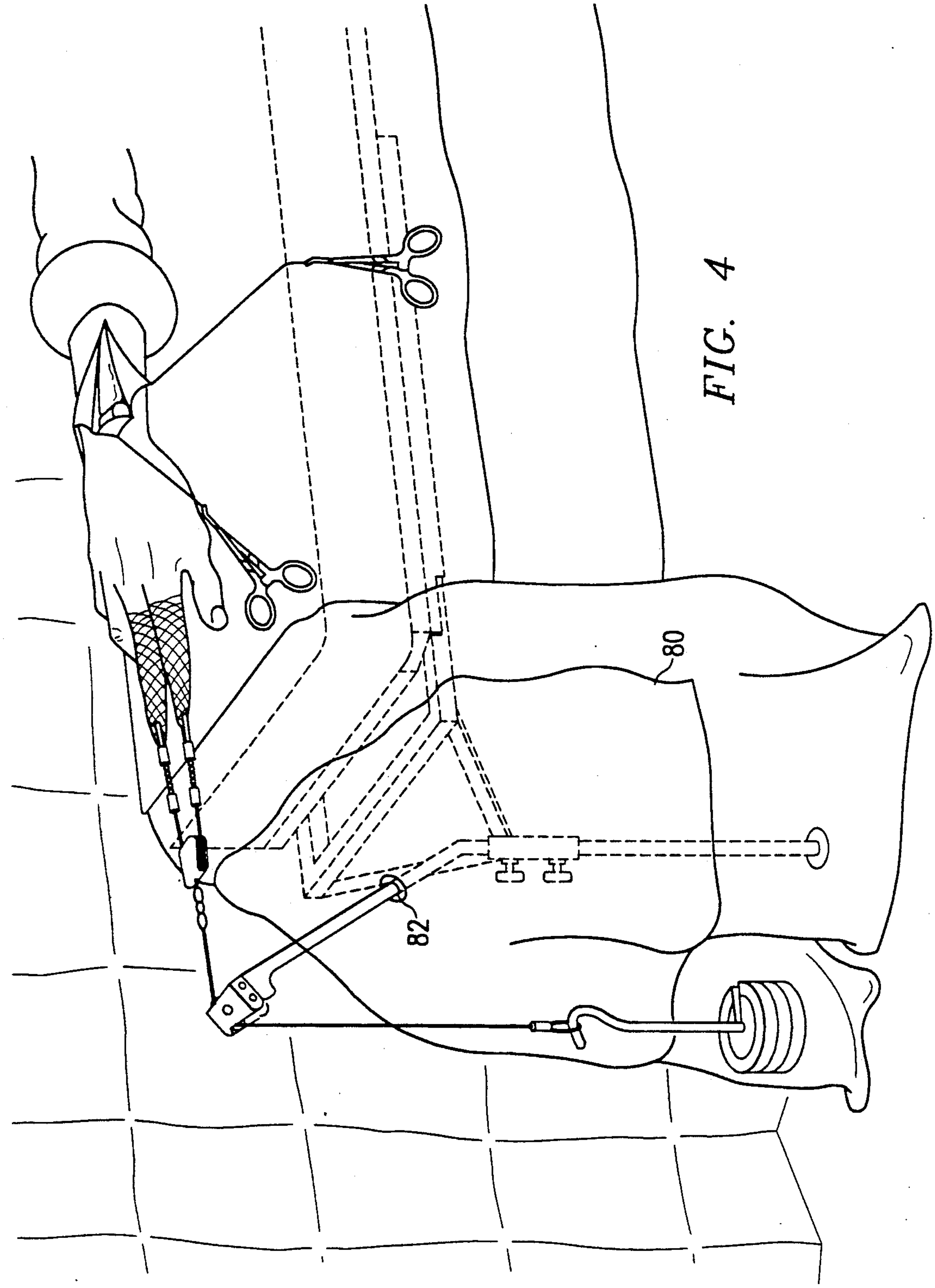
FIG. 4 is a plan view of the hand traction surgical table of the present invention in use.

As set forth above, cable 52, pulley 48, and arm 47 are preferably constructed of stainless steel whereby they can be sterilized. A surgical drape 80 having a hole 82 formed therethrough is preferably mounted over hand traction surgical table 10 as depicted in FIG. 4. In this way, the hand and forearm of the patient can be isolated from the remaining elements of table 10.

Although the present invention has been disclosed herein with respect to specific preferred embodiments, it will be appreciated by those of ordinary skill in the art that modifications can be made without departing from the true spirit and scope of the invention.

What is claimed is:

1. A hand traction surgical table for retaining a hand and a forearm in a predetermined position in order to facilitate surgical procedures thereon comprising:
   - a surgical table frame;
   - an arm board having an upper surface and a lower surface, said arm board mounted on said surgical table frame whereby said hand and said forearm can rest on said upper surface of said arm board;
   - a pulley device comprising a base and a pulley mounted on said base, said base of said pulley device mounted on said surgical table frame;
   - a cable mounted through said pulley of said pulley device, said cable having a first end and a second end;
   - a finger retention device mounted at said first end of said cable; and
   - a force applicator mounted at said second end of said cable whereby a predetermined reduction force can be applied to said hand and forearm through said cable.

2. The hand traction surgical table of claim 1, further comprising an arm board pad mounted on said upper surface of said arm board whereby said hand and said forearm can rest on said arm board pad.

3. The hand traction surgical table of claim 2, wherein said arm board is releasably mounted on said upper surface of said arm board.

4. The hand traction surgical table of claim 1, wherein said force applicator comprises a force application platform mounted at said second end of said cable and a plurality of weights whereby said weights can be mounted on said force application platform in order to apply a predetermined force to said cable.

5. The hand traction surgical table of claim 1, wherein said finger retention device comprises a Chinese finger trap.

6. The hand traction surgical table of claim 1, wherein said finger retention device comprises a plurality of Chinese finger traps.

7. The hand traction surgical table of claim 1, wherein said finger retention device comprises a finger retention pulley mounted at said first end of said cable, a finger retention cable mounted through said finger retention pulley, said finger retention cable having a first end and a second end, and a pair of Chinese finger traps disposed at said first end and at said second end of said finger retention pulley.

8. The hand traction surgical table of claim 1, wherein said arm board can be detachably mounted on said surgical table frame.

9. The hand traction surgical table of claim 1, wherein said pulley device and said cable are constructed of stainless steel.

10. The hand traction surgical table of claim 1, wherein said pulley device and said cable are constructed of a sterilizable material.

11. The hand traction surgical table of claim 1, wherein said hand traction surgical table can be attached to a primary surgical table.

12. A hand traction surgical table for retaining a hand and a forearm in a predetermined position in order to facilitate surgical procedures thereon comprising:

a surgical table frame have a pair of support arms, a support leg, and a connector whereby said support leg can be selectively positioned in said connector;

an arm board rest mounted on said pair of support arms of said surgical table frame, said arm board having an upper surface and a lower surface whereby said hand and said forearm can rest on said upper surface of said arm board;

a pulley device adjustably mounted through said connector of said surgical table frame, said pulley device comprising a base and a pulley mounted on said base, said base mounted on said connector of said frame;

a cable mounted through said pulley of said pulley device, said cable having a first end and a second end;

a finger retention pulley mounted at said first end of said cable;

a finger retention cable mounted through said finger retention pulley, said finger retention cable having a first end and a second end;

a first finger retention device disposed on said first end of said finger retention cable and a second finger retention device mounted on said second end of said finger retention cable; and a force applicator mounted at said second end of said cable whereby a predetermined force can be applied to said hand and said forearm through said cable.

13. The hand traction surgical table of claim 12, wherein said surgical table frame and said arm board are constructed of a radiotransparent material.

* * * * *